United States Patent [19]

Nornberg et al.

[11] Patent Number: 5,203,943
[45] Date of Patent: Apr. 20, 1993

[54] METHOD OF FORMING INTERNAL STRICTURES IN A TUBULAR MEMBER AND A BONDING CONNECTION WITH AN INSERTED TUBE

[75] Inventors: Jon M. Nornberg, Woodbury; Raymond L. Ferguson, St. Paul; David M. Stoen, Mahtomed, all of Minn.

[73] Assignee: Minnesota Mining and Manufacturing Company, Saint Paul, Minn.

[21] Appl. No.: 626,826

[22] Filed: Dec. 13, 1990

[51] Int. Cl.⁵ .................. F16L 13/02; B32B 31/00
[52] U.S. Cl. .................... 156/245; 156/293; 285/21; 285/423; 285/915
[58] Field of Search ............... 285/21, 22, 423, 238, 285/369, 915; 264/320, 322; 156/245, 293

[56] References Cited

U.S. PATENT DOCUMENTS

| | | | |
|---|---|---|---|
| Re. 31,404 | 10/1983 | Anger | 264/573 |
| 3,128,504 | 4/1964 | Gewecke | 18/36 |
| 3,989,280 | 11/1976 | Schwarz | 285/21 |
| 3,994,515 | 11/1976 | Cotten | 285/21 |
| 3,997,195 | 12/1976 | Bartholomew | 285/423 X |
| 4,064,206 | 12/1977 | Seufert | 264/26 |
| 4,127,632 | 11/1978 | Anger | 264/94 |
| 4,137,117 | 1/1979 | Jones | 285/21 X |
| 4,181,549 | 1/1980 | McPhee | 156/146 |
| 4,229,028 | 10/1980 | Gray | 285/423 X |
| 4,256,333 | 3/1981 | Jones | 285/22 |
| 4,353,522 | 10/1982 | Anger | 249/144 |
| 4,382,753 | 5/1983 | Archibald | 417/479 |
| 4,396,816 | 8/1983 | Krishnakumar et al. | 219/10.43 |
| 4,410,322 | 10/1983 | Archibald | 604/153 |
| 4,521,178 | 6/1985 | Anger | 425/548 |
| 4,576,671 | 3/1986 | Shimanaka | 156/245 |
| 4,758,386 | 7/1988 | Fanning | 264/1.5 |
| 4,880,580 | 11/1989 | Bowers et al. | 264/26 |
| 4,900,389 | 2/1990 | Schnell et al. | 156/273.7 |
| 4,902,269 | 2/1990 | Susimi et al. | 493/380 |
| 4,940,870 | 7/1990 | Shibata et al. | 219/10.491 |
| 4,943,224 | 7/1990 | Nied et al. | 425/174.8 |

FOREIGN PATENT DOCUMENTS

| | | | |
|---|---|---|---|
| 289831 | 11/1988 | European Pat. Off. | 285/915 |
| 1112326 | 5/1968 | United Kingdom | 285/915 |

Primary Examiner—Dave W. Arola
Attorney, Agent, or Firm—Armstrong, Teasdale, Schlafly & Davis

[57] ABSTRACT

A leak-resistant connection between two generally tubular members in which second tubular member is telescopically received in a first generally tubular member. There is at least one integral continuous annular stricture formed in the lumen of the first tubular member for engaging and sealing with the second tubular member. A second, integral stricture of larger profile may be provided as a stop to abut the end of the second tubular member. A method of making the connection is also disclosed. The method includes the step of forming the strictures in the tubular member by inserting a grooved mandril into the lumen of the tubular member and heating and applying pressure to the tubular member to form the strictures in the grooves in the mandril. The tubular member can be conveniently heated with RF energy applied through the mandril.

21 Claims, 2 Drawing Sheets

METHOD OF FORMING INTERNAL STRICTURES IN A TUBULAR MEMBER AND A BONDING CONNECTION WITH AN INSERTED TUBE

BACKGROUND OF THE INVENTION

This invention relates to a leak resistant connection between tubular members in a fluid transport system, to an end construction for tubular members in such a system, and to a method of making a connection between tubular members in a fluid transport system.

Fluid transport systems typically comprise a number of interconnected components. In most systems it is important that the connections between components be strong, reliable, and leak free. This is particularly true in medical applications, for example an intravenous fluid delivery system. Leakage in such a system might mean that a patient would not get adequate medication, and that health care workers could be exposed to the leaked medications. Leakage could also result in the aspiration of gas into the fluid delivery system. Moreover, the integrity and reliability of the connections are becoming increasingly important as the use of pressure infusion becomes more common, because the entire fluid system is under pressure. For example, the connection between the delivery tubing and the infusion pump cassette of the type disclosed in Archibald, U.S. Pat. No. 4,382,753 is under pressure as the infusion pump pumps fluid through the system.

While the integrity of the connections is important, it is also important that the fabrication process be relatively simple, inexpensive, and reliable, to minimize the cost to the patient. This is particularly true for intravenous tubing which is typically made for a single use, and cannot be reused.

SUMMARY OF THE INVENTION

The present invention provides a reliable and leak resistant connection between two generally tubular members in a fluid transport system. The invention also provides a method for making such a connection that is fast, simple, and easy, so that the connection is economical. The present invention also provides an improved construction for a tubular member adapted for use in a fluid transport system, to facilitate the formation of a leak resistant connection. Finally, the present invention provides a method for making the improved tubular member.

The connection of the present invention is of the type in which a first generally tubular member telescopingly receives the end of a second generally tubular member. There is at least one continuous annular stricture inside the lumen of the first tubular member, adjacent the end. The stricture engages the exterior of the portion of the second tubular member that is inside the lumen of the first tubular member. The stricture in the lumen of the first tubular member acts like an integral o-ring, assuring continuous contact between the first and second tubular members. However, the end of the second tubular member can be easily inserted into the first tubular member to make the connection. The overlapping portions of the first and second tubular members are preferably joined, for example by solvent welding.

The connection may also include a second continuous annular stricture inside the lumen of the first generally tubular member. The second stricture is spaced further from the end than the first stricture, and projects further into the lumen than the first stricture. The second stricture abuts the end of the second tubular member inside the first tubular member, forming a positive stop that limits how far the second tubular member can be inserted into the first tubular member. The inventors believe that the connection has improved mechanical strength over connections without strictures.

The method of the present invention of making the connection between two generally tubular members comprises the steps of forming at least one continuous annular stricture in the lumen of the first tubular member, and inserting the end of the second tubular member into the end of the first tubular member, beyond the structure. The tubular members may be joined, for example with solvent welding. The method may further comprise the step of forming a second continuous annular stricture in the lumen of the first tubular member. The second stricture is spaced further from the end than the first stricture, and projects further into the lumen than the first stricture so that it can abut the end of the second tubular member. The end of the second tubular member is inserted into the lumen of the first tubular member, past the first stricture, until it abuts the second stricture.

The step of forming the first and second strictures in the lumen of the first tubular member preferably comprises the steps of inserting a mandril, having at least one circumferential annular groove therein, into the end of the lumen of the first tubular member. The portion of the first tubular member surrounding the mandril is heated to form an annular projection on the inside wall of the first tubular member, in the groove in the mandril. The mandril is then removed, and the annular projection on the wall of the first tubular member forms continuous annular stricture in the lumen. The method may further comprise the step of pressing the portion of the first tubular member surrounding the mandril against the mandril, to facilitate the formation of the annular strictures in the grooves in the mandril. This can be conveniently done with one or more dies. The step of heating the first generally tubular member may be done by applying RF energy to the tubular member. If a die is used to press the tubular member against the mandril, the die provides a convenient second pole for applying RF energy to the tubular member to heat it.

The improved construction for a tubular member adapted for use in a fluid transport system comprises at least one continuous annular stricture inside the lumen of the tubular member, adjacent the end. The stricture forms a sealing member for engaging the exterior of a second tubular member inserted into the lumen. The construction may include a second continuous annular stricture inside the lumen of the tubular member, spaced further from the end than the first stricture. The second stricture projects further into the lumen than the first stricture, forming a stop for abutting the end of a second tubular member inserted into the lumen.

According to the method of making the improved tubular member, a mandril, having at least one circumferential annular groove therein, is inserted into the end of the lumen of the tubular member. The portion of the tubular member surrounding the mandril is heated to form an annular projection on the inside wall of the tubular member, in the groove in the mandril. The mandril is then removed from the lumen, and the annular projection on the wall of the tubular member forms continuous annular stricture in the lumen of the tubular member. The method of making the improved tubular member may further comprise the step of pressing the portion of the tubular member surrounding the mandril against the mandril, to facilitate the formation of the annular strictures in the grooves in the mandril. This can be conveniently done with one or more dies. The step of heating the tubular member may be done by applying RF energy to the tubular member. If a die is used to press the tubular member against the mandril, the die provides a convenient second pole for RF heating of the tubular member.

The connection of the present invention is reliable and leak resistant. The first continuous annular stricture in the first tubular member provides continuous contact with a second tubular member inserted therein, facilitating a leak-resistant connection, yet allows the second tubular member to be easily inserted into the first tubular member. The second continuous annular stricture provides a positive stop, facilitating the quick yet accurate insertion of the second tubular member into the first tubular member. The method for making the connection is fast, simple, and easy, so the connection is economical. The improved construction for a tubular member of this invention, for the reasons discussed above, is particularly adapted to form leak resistant connections. And, like the method for making the connection, the method for making the construction is fast, simple, and easy.

These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figure 1:
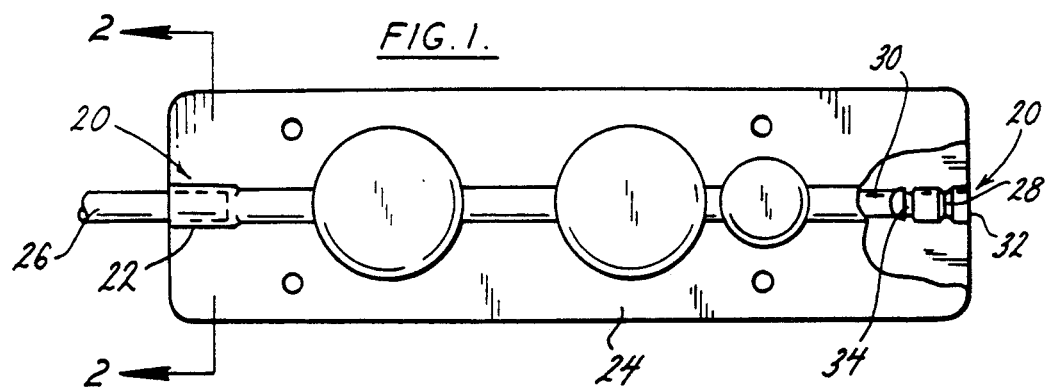
FIG. 1 is a top plan view of an infusion pump cassette having a connection according to the principles of this invention at one end, and having portions broken away at the other end to illustrate the formation of the connection.
Figure 2:
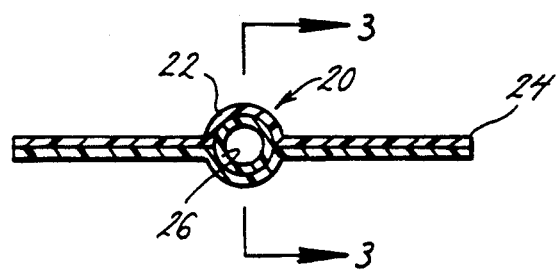
FIG. 2 is a transverse cross-sectional view of the connection taken along the plane line 2—2 in FIG. 1.
Figure 3:
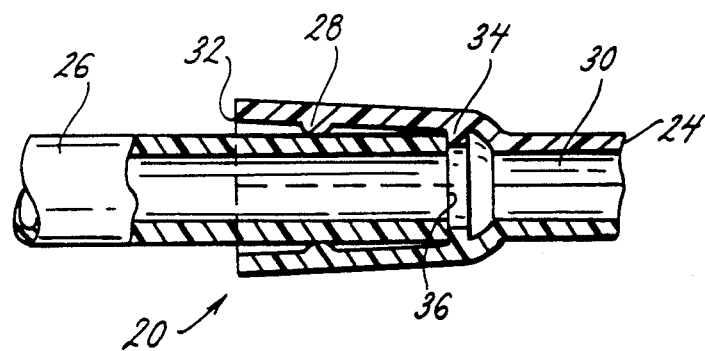
FIG. 3 is a longitudinal cross-sectional view of the connection taken along the plane of line 3—3 in FIG. 2.

An embodiment of a connection between two generally tubular members according to the principles of this invention is shown in FIGS. 1-3. As shown on the left side of FIG. 1, the connection, indicated generally as 20, is between a first generally tubular member—a socket 22 on an infusion pump cassette 24, and a second generally tubular member—the end of an intravenous line 26. Although this description of the preferred embodiment refers to infusion pump cassette 24 and intravenous line 26, the invention is not so limited, and applies to connections between any two generally tubular members in a fluid transport system.

The cassette 24 is preferably made from a thermoplastic material, such as polyvinyl chloride. The cassette 24 shown in FIG. 1 is of the type disclosed in Archibald, U.S. Pat. No. 4,382,753, incorporated herein by references, in which the sockets 22 are formed between top and bottom generally planar pieces that are heat-sealed or otherwise joined together. Although the sockets 22 are formed between two planar members, they each have a generally tubular configuration. The intravenous line 26 may also be made of a thermoplastic material, such as polyvinyl chloride tubing. Both the socket 22 and the intravenous line 26 are preferably made from a solvent-weldable material.

Figure 4:
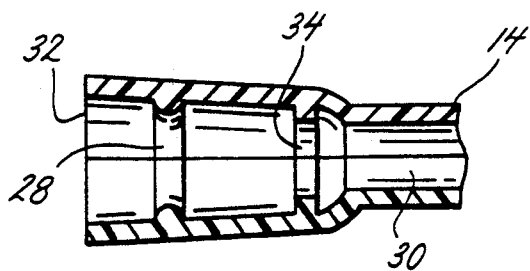
FIG. 4 is a longitudinal cross-section view of an end construction for tubular member adapted for use in connections according to the principles of this invention.

As shown on the right side of FIG. 1, and in FIGS. 3 and 4, the connection 20 between the socket 22 and the intravenous line 26 comprises at least one continuous annular stricture 28 inside the lumen 30 of the socket 22, adjacent the end 32. The stricture 28 is formed integrally with the wall of the socket 22, and projects into the lumen 30, forming an o-ring like sealing member that engages the exterior of a portion of the intravenous line 26 extending inside the lumen 30 of the socket 22. (See FIG. 3). The stricture 28 assures continuous contact between the socket 22 and the intravenous line 26 around the circumference of the socket, resisting leakage between the socket 22 and the intravenous line 26. The overlapping portions of the socket 22 and the intravenous line 26 are preferably solvent-welded together, for example with cyclohexanone. Of course it would be possible to bond the socket 22 and the intravenous line 26 together in some other manner, for example with adhesive or by heat-welding.

As shown on the right side of FIG. 1, and in FIGS. 3 and 4, the connection 20 preferably further comprises a second annular stricture 34 inside the lumen 30 of the socket 22. The second stricture 34 is spaced further from the end 32 of the socket 22 than the first stricture 28. The second stricture projects further into the lumen 30 than the first stricture 28, projecting far enough into the lumen 32 to abut the end 36 of the intravenous line 26, limiting how far the end 36 of the intravenous line 26 can be inserted into the lumen 30 of the socket 22. (See FIG. 3). Of course, since the second stricture 34 functions as a stop, it does not have to be continuous, although it preferably is. The socket 22 and the intravenous line 26 are preferably sized so that the socket 22 must stretch slightly to accommodate the end of the intravenous line 26, to achieve a tight fit and cause the stricture 28 in the socket 22, to be held snugly against the exterior of the tube 22. (Compare FIGS. 3 and 4).

The method of this invention of making a connection between the ends of first and second generally tubular members comprises the step of forming at least one continuous annular stricture in the lumen of the first tubular member. The second tubular member is then telescopingly inserted into the lumen. The two tubular members are then bonded together, preferably by solvent-welding. A suitable solvent, for example cyclohexanone, is applied to at least one of, and preferably both, the interior of the first generally tubular member and the exterior of the second tubular member. Then, the end of the second tubular member is inserted into lumen of the first tubular member, and the two members are held together for a sufficient time for solvent welding to occur.

The method preferably also comprises the step of forming a second continuous annular stricture in the lumen of the first tubular member, spaced further from the end than the first stricture. The second stricture has a higher profile than the first stricture, i.e., it projects further into the lumen than the first stricture, sufficiently to abut the end of the second tubular member, when the second tubular member is inserted into the lumen of the first tubular member. Then, when the second tubular member is inserted into the lumen of the first tubular member, it is advanced past the first stricture until its end abuts the second stricture.

In the context of the connection 20 between the socket 22 of the cassette 24 and the intravenous line 26, the first stricture 28 (and preferably the second stricture 34) are formed in the socket 22. The socket 22 and the intravenous line 26 are then bonded together. Preferably, solvent is applied to the interior of the socket 22 and to the exterior of the intravenous line 26. The intravenous line 26 is then inserted into the socket, so that the end 36 passes the first stricture 28 and abuts the second stricture 34. The tubular members are held in place until the ends weld together.

Figure 6:
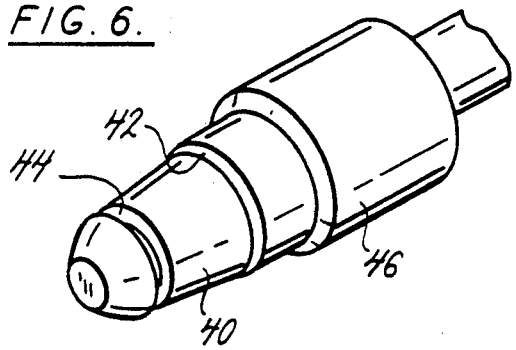
FIG. 6 is a perspective view of the head of the mandril.
Figure 5:
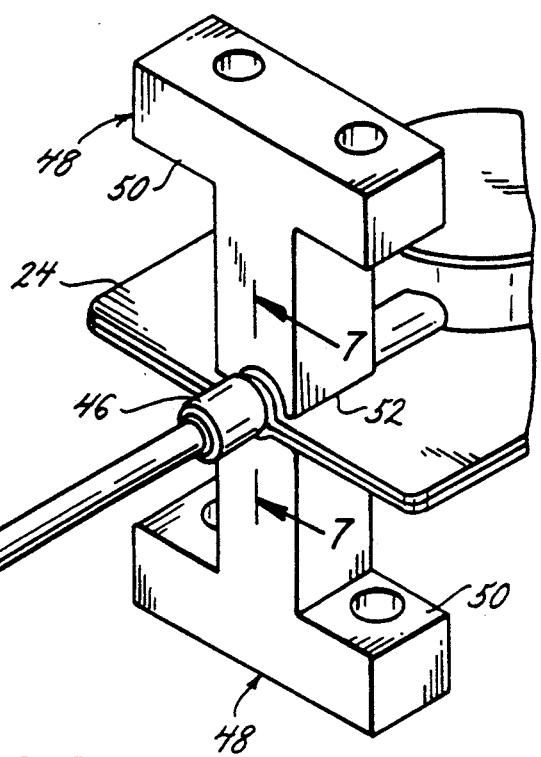
FIG. 5 is a perspective view of the mandril and dies as they are used to form the connection according to the principles of this invention.
Figure 7:
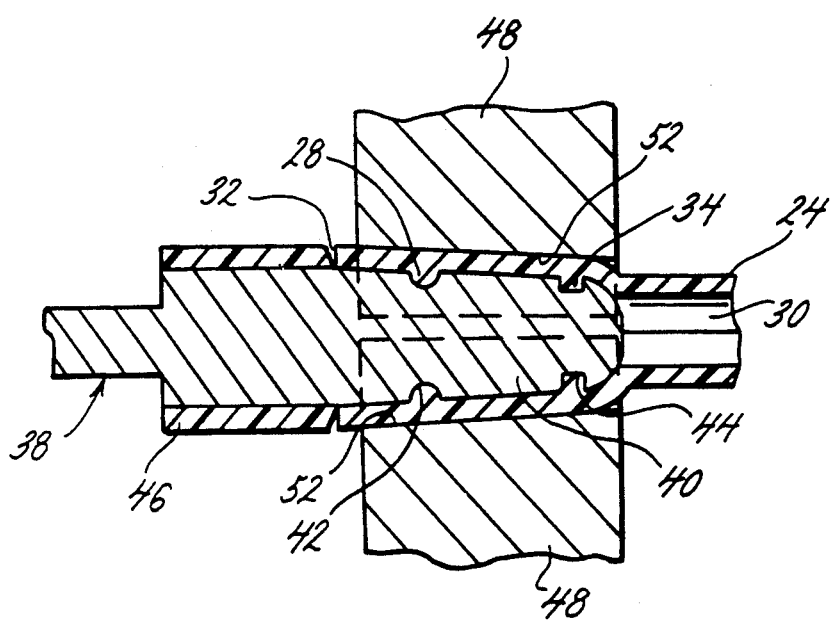
FIG. 7 is a cross-sectional view of the mandril and the dies taken along the plane of line 7—7 in FIG. 5.

In the preferred embodiment of this method, as shown in FIGS. 5 and 7, the step of forming the strictures 28 and 34 in the first tubular member comprises inserting a mandril 38 into the lumen 30 of the first tubular member, i.e., the socket 22. As shown in FIG. 6 and 7, the mandril 38 preferably has a tapered distal tip 40, to facilitate the insertion and removal of the tip 40 from the lumen 30. The tip 40 has at least one groove 42 which, as described below, serves as a mold for the first stricture 28. The sides of the groove 42 are preferably curved or chamfered (see FIG. 7), so that the groove 42 forms the stricture 28 with a sloped leading edge (see FIG. 4) to permit the end 36 of the intravenous line 26 to be easily inserted past the stricture 28, even though the stricture projects sufficiently into the lumen to engage the exterior of the intravenous line 26. The tip 40 of the mandril 38 preferably also has a second groove 44 which, as described below, serves as a mold for the second stricture 34. The second groove 44 is located closer to the distal end of the mandril 38 than the first groove 42. The groove 44 is deeper than the groove 42, and the sides of the groove 44 are preferably substantially vertical (see FIG. 7), so that the groove forms the stricture 34 with a flat leading edge (see FIG. 4) to abut the end 36 of the intravenous line 26. The mandril 38 is preferably made of a conductive material, for example brass. The mandril 38 preferably includes a collar 46 that limits how far the tip 40 of the mandril can be inserted into the lumen 30 of the first tubular member. The collar 46 is preferably made of a non-conductive substance, for example Delrin.

After the grooved tip 40 of the mandril 38 is inserted into the lumen 30 of the first tubular member, the portions of the tubular member surrounding the tip of the mandril are heated. This causes the wall of the first tubular member to soften and to conform to the grooved tip 40 of the mandril, forming annular projections on the interior wall of the tubular member, in the grooves 42 and 44. (See FIG. 7). When the mandril is removed from the lumen, there are two raised projections in the lumen forming continuous annular strictures 28 and 34.

The method of forming the stricture preferably further comprises the step of pressing the portion of the tubular member surrounding the tip of the mandril against the mandril to facilitate the formation of the strictures 28 and 34 by forcing the material forming the wall of the tubular member into the grooves 42 and 44 on the mandril. This can be conveniently done by compressing the portions of the tubular member with a die, and in this preferred embodiment a pair of mating dies 48, as shown in FIGS. 5 and 7. Each die 48 has flanges 50 at its base for mounting a die on a jig. Each die 48 also has a recess 52 for receiving and engaging a portion of the tubular member, and urging the tubular member against the tip of the mandril. As shown in FIG. 7, the recess 52 is preferably tapered complementary to the taper of the tip 40 of the mandril 38. The dies 48 are preferably made from a conductive material, for example brass. The pair of dies 48 are particularly suited to forming the connection in a socket 22 on a cassette, because the dies define a space between for accommodating the web of the cassette 24. (See FIG. 5). However, when forming a connection with some other tubular member, a single die, or more than two dies may be more suitable.

The tubular member can be conveniently heated by applying RF energy to the material via the mandril 38. The dies 48 form a convenient second pole for the application of RF energy to the portions of the tubular member surrounding the tip of the mandril.

The improved end construction for a tubular member adapted for use in a fluid transport system to facilitate leak resistant connection with a second tubular member is shown in longitudinal cross-section in FIG. 4. As shown, the construction is incorporated in a socket 22 of a infusion pump cassette 24, although as discussed above the invention is not so limited. The construction comprises a first continuous annular stricture 28 in the lumen 30 of the socket, adjacent the end 32. The first stricture 28 forms a sealing member, similar to an integral o-ring, for engaging the exterior of a second tubular member inserted into the lumen 30. The construction preferably also comprises a second stricture 34, spaced further from the end 32 than the first stricture 28, and projecting further into the lumen 30 than the first stricture. The second stricture 34 forms a stop for abutting the end of a second tubular member inserted into the lumen 30.

The end construction is formed as described above with respect to making the connection 20.

OPERATION

In operation, connections according to this invention have been made as follows: A mandril 38 is provided with a tip 40 that tapers from an outside diameter of 0.156 inches (0.40 cm) to an outside diameter of 0.120 inches (0.31 cm) in a six degree taper. The first groove 40 was machined to a depth of 0.007 inches (0.02 cm), and the second groove 42 was machined depth of 0.012 inches (0.03 cm). The tip 40 of the mandril 38 was inserted into the socket 22 of an infusion pump cassette 24. The cassette 24 is made from polyvinyl chloride, and the socket 22 had an inside diameter such that the tip 40 stretches the socket slightly. Two opposing dies 48, each having a recess 52, complementary to the taper of the tip 40 of the mandril 38, were mounted on jigs, and closed around the tip of the mandril, to compress the wall of the socket 22 against the tip 40 of the mandril 38, and urge material from the wall of the socket into the grooves 40 and 42. (See FIGS. 5 and 7).

The mandril 38 and the dies 48 are connected to an RF generator, for example a Thermatron model KF-82 generator from Thermex Corp., Bay Shore, New York. The generator is activated at a setting of 045, and maintained for 1.0 seconds with the two poles being the two dies 48, in order to reinforce the socket 22. The generator is then activated a second time at a power setting of 032, and maintained for 0.75 seconds, with one pole being the mandril 38 and the other pole being the dies 48. The socket 22 is allowed to cool for two seconds before the mandril 38 is removed.

A length of polyvinyl chloride tubing 26 with an inner diameter of 0.120 inches (0.31 cm) and an outer diameter of 0.162 inches (0.41 cm) is then dipped into a beaker of cyclohexanone, and inserted into the socket 22 until its end 36 abutted the second stricture 34. The tubing 26 and the socket 22 are sized so that the socket is slightly stretched during this insertion. (See FIG. 3). The tubing and the socket are left undisturbed to permit solvent welding to occur, bonding the tubing 26 in the socket 22.

A lot of 6000 connections formed in this manner was tested by immersing the connections and pressuring the connections to a pressure of 10 p.s.i. No leaks were detected in the lot.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limited sense.

What is claimed is:

1. A method of making a connection between the ends of first and second generally tubular members, the method comprising:
    forming at least one continuous annular stricture in the lumen of the first tubular member by inserting a mandril, having at least one circumferential annular groove, into the end of the lumen of the first tubular member; heating the portion of the first tubular member surrounding the mandril to form an annular projection in the groove in the mandril; and removing the mandril from the lumen leaving an annular stricture in the lumen of the first tubular member;
    inserting the end of the second tubular member into the end of the first tubular member, beyond the stricture, and
    bonding the first and second tubular members together.

2. The method of claim 1 wherein the step of bonding the first and second tubular members comprises the steps of applying a solvent to at least one of the interior of the end of the first tubular member and the exterior of the end of the second tubular member before inserting the second tubular member into the first tubular member.

3. The method according to claim 1 wherein the step of heating the first tubular member comprises applying RF energy to the tubular member.

4. The method according to claim 3 wherein the step of heating the first tubular member comprises applying RF energy to the tubular member with the mandril.

5. The method according to claim 1 further comprising the step of pressing the portion of the first tubular member surrounding the mandril against the mandril while heating the first tubular member.

6. The method according to claim 5 wherein the step of pressing the first tubular member against the mandril includes pressing the tubular member against the mandril with at least one die.

7. The method according to claim 1 wherein the portion of the mandril that is inserted into the tubular member is generally tapered.

8. A method of making a connection between the ends of first and second generally tubular members, the method comprising:
    forming a first continuous annular stricture in the lumen of the first tubular member, and a second annular stricture in the lumen of the first tubular member, spaced further from the end of the first tubular member than the first stricture, and having a higher profile than the first stricture to abut the end of the second tubular member inserted into the lumen by inserting a mandril, having at least two axially spaced circumferential annular grooves therein, into the end of the lumen of the first tubular member; heating the portion of the first tubular member surrounding the mandril to form an annular projection in each groove in the mandril; and removing the mandril from the lumen leaving two annular strictures in the lumen of the first tubular member;
    inserting the end of the second tubular member into the end of the first tubular member, beyond the first stricture, until the end of the second tubular member abuts the second stricture, and
    bonding the first and second tubular members together.

9. The method according to claim 8 further comprising the step of pressing the portion of the first tubular member surrounding the mandril against the mandril while heating the first tubular member.

10. The method according to claim 9 wherein at least two dies are used to press the first tubular member against the mandril, each die having a recess therein generally complementary to the configuration of the portion of the mandril inserted into the tubular member.

11. The method according to claim 10 wherein the portion of the mandril that is inserted into the first tubular member is generally tapered, and wherein the recesses in the dies have a complementary taper.

12. The method according to claim 8 wherein the groove closest to the distal end of the mandril is deeper than the groove closest to the proximal end of the mandril, to form said stricture with said higher profile.

13. The method according to claim 8 wherein the step of bonding the first and second tubular members comprises the step of applying a solvent to at least one of the interior end of the first tubular member and the exterior end of the second tubular member before inserting the second tubular member into the first tubular member.

14. A method of making an improved tubular member for facilitating leak-resistant connections with other tubular members, the method comprising the steps of:
    inserting a mandril having an annular groove into the end of the lumen of the tubular member;
    heating the portion of the tubular member surrounding the mandril to form an annular projection in the grove in the mandril, and removing the mandril from the lumen to leave a continuous annular stricture in the lumen of the tubular member.

15. The method according to claim 14 wherein the step of heating the tubular member comprises applying RF energy to the tubular member.

16. The method according to claim 14 further comprising the step of pressing the portion of the tubular member surrounding the mandril against the mandril while heating the tubular member.

17. The method according to claim 16 wherein the step of pressing the tubular member against the mandril includes pressing the tubular member against the mandril with at least one die having a recess therein generally complementary to the configuration of the portion of the mandril inserted into the tubular member.

18. The method according to claim 17 wherein the portion of the mandril that is inserted into the tubular member is generally tapered, and wherein the recess in the die is tapered.

19. The method according to claim 17 wherein the step of heating the tubular member comprises applying RF energy to the tubular member with the mandril and the die.

20. The method according to claim 14 wherein the portion of the mandril inserted into the tubular member has two axially spaced circumferential annular grooves therein for forming two annular strictures in the tubular member.

21. The method according to claim 20 wherein the groove closest to the distal end of the mandril is deeper than the groove closest to the proximal end of the mandril, to form a stricture with a higher profile.

* * * * *